(12) United States Patent
Wu et al.

(10) Patent No.: US 8,637,035 B2
(45) Date of Patent: Jan. 28, 2014

(54) ANTI-DENGUE VIRUS ANTIBODIES

(75) Inventors: Han-Chung Wu, Taipei (TW); Pi-Chun Li, Banqiao (TW); Mei-Ying Liao, Wufeng Township (TW); Chien-Yu Chiu, Taipei (TW)

(73) Assignee: Academia Sinica, Taipei (TW)

( * ) Notice: Subject to any disclaimer, the term of this patent is extended or adjusted under 35 U.S.C. 154(b) by 159 days.

(21) Appl. No.: 13/182,771

(22) Filed: Jul. 14, 2011

(65) Prior Publication Data

US 2012/0014945 A1    Jan. 19, 2012

Related U.S. Application Data

(60) Provisional application No. 61/364,845, filed on Jul. 16, 2010.

(51) Int. Cl.
*A61K 39/42* (2006.01)
*A61K 39/12* (2006.01)
*G01N 33/53* (2006.01)

(52) U.S. Cl.
USPC ........... 424/159.1; 424/218.1; 435/5; 435/7.1

(58) Field of Classification Search
None
See application file for complete search history.

*Primary Examiner* — Stacy B. Chen
(74) *Attorney, Agent, or Firm* — Cesari and McKenna, LLP

(57) ABSTRACT

Provided herein are monoclonal antibodies specific to dengue virus as well as their antigen-binding fragments, and functional variants. Also disclosed are uses thereof for treating or diagnosing dengue virus infection.

15 Claims, 2 Drawing Sheets

```
                              FR1                              CDR1              FR2                    CDR2
DB2-3   (SEQ ID NO:13)  EVQLQQSGAELVRPGVSVKISCKGSG  YTFTDYAIT   WVKESHAKSLEWI   GLISTYGDSFYNQKFKG
DB13-19 (SEQ ID NO:14)  EVKLVESGGGLVKPGGSLKLSCATSG  FTFSTYGMS   WVRQTPEKRLEWV   ATISGDGSYTYYPDTVKGRF
DB23-3  (SEQ ID NO:15)  EVQLQQSGSELVRPGVSVKISCKGSG  YTFTDYAH    WVRQSHDKSLEWI   GLISTYYGDVSTNQKFKGKA
DB25-2  (SEQ ID NO:16)  QVQLKESGPGLVQPSQSLSITCVSG   FSLTDYGVH   WIRQSPGKGLEWLG  VIWRGGITDYNAAFMS
DB32-6  (SEQ ID NO:1)   QVQLQQSGAELVKPGASVKLSCCASG  FNIKDTYIH   WVKQRPGQGLEWI   GRIDPENGNAKYDPNFQAKA
DB42-3  (SEQ ID NO:17)  EVKLVESGGDLVKPGGSLKLSCAASG  FTFSNFAMS   WVRQTPEKRLEWV   ATIGGGDSYFPDSVKGRF

FR3                              CDR3                     FR4
DB2-3                   KATMTVDKSSRTAVMELARLTSEDSAIYYC   TIRDGKGAMDY     WGQGTSVTVSS
DB13-19                 TISRDNAKNNLYLQMSSLRSEDTALYYC     ASYNYGGFAY      WGQGTLVSVSAAKTTPPSDYPLA
DB23-3                  TTVDKSSSTAYLELARLTSEDSAIYYC      ARLGGDFFADY     WGQGTSVTVSSAKTTPPSDYPLA
DB25-2                  RLSITKDNSKSQVFFKMDSLQPDDSAIYYC   AKNFGTHYYGSNYGNFDY  WGQGTTLTVSS
DB32-6                  TITADTSSNTAYLHLSSLTSEDTAVYYS     VRTGSFWYFDV     WGAGTTVTVSS
DB42-3                  TISRDNARNILYLQMSSLRSDDTAMYFC     TREGDDDQYYYSMDY WGQGTSVTVSSAKTTPPSDYPLA
```

(B)

```
                              FR1                              CDR1              FR2                    CDR2
DB2-3   (SEQ ID NO:18)  DVVMTQTPLSLPVSLGDLASISC   RSSQSLVHSNGNTYLH   WYLQKPGQSPKLLIY   KVSNRFS
DB13-19 (SEQ ID NO:19)  DIVMTQSHKFMSTSVGDRVSITC   KASQDVGIAVA        WYQQKFRQSPKLLIY   WASTRHT
DB23-3  (SEQ ID NO:20)  DVLTQTPLSLPVSLGDQASISC    RSSQSVVNSNGNTYLE   WYLQKPGQSPKLLIY   KVSNRFS
DB25-2  (SEQ ID NO:21)  VVMTQTPKFLLVSAGDRVTITC    KASQSVSNDVA        WYQQKPGQSPKLLIY   YVSNRYS
DB32-6  (SEQ ID NO:5)   DIVLTQSPASLAVSLGQRATISC   RASESVDKYGITFLN    WFQQKPGQPPKLLIH   SASNRGS
DB42-3  (SEQ ID NO:22)  QAVVTQESALTTSPGETVLITC    RSSTGAVTTSNYAN     WVQEKPDRLFNGLIG   GTNNRAP

FR3                              CDR3                     FR4
DB2-3                   GVPDRFSGSGSGTNFTLKISRVEAEDLGVYFC   SQSTHVPYT     GGGTKLEIK
DB13-19                 GVPDRFTGSGSGTDLLTINNVQSEDLADYFC    QQFNSYPLT     FGGGTKLEIKRADAAPTVS
DB23-3                  GVPDRFSGSGSGTDFTLKISRVEAEDLGVYFC   FQGSHFPRT     FGGGTKLEIKRADAAPTVS
DB25-2                  GVPDRFTGSGYGTDFTFTINTVQAEDLAVIFC   QQDYSSPYT     FGGGTKLEIK
DB32-6                  GVPARFSGSGSGTDFSLNIHPMEEDDIAMYFC   QQSKEVPWT     FGGGTKLEIK
DB42-3                  GVPARFSGSLIGDKAALTITGAQPEDEAIYFC   ALWYSNHFWV    FGGGTKLTVLGQPKSTPLT
```

FIG. 2

| DB32-6 phage clones (12 aa) | Peptide Sequences |
|---|---|
| PC32-1, 12 (SEQ ID NO:23) | F H K E Y H I T R M T A |
| PC32-7, 9 (SEQ ID NO:24) | T H K E Y H T L M G L Q |
| PC32-4, 11, 13, 18 (SEQ ID NO:25) | Y H K E W H G S L L A R |
| PC32-2, 5, 8, 14, 16, 17 (SEQ ID NO:26) | N H K T W H L Q V N P L |
| PC32-6, 10, 20 (SEQ ID NO:27) | T H K L W H I P S N W R |

| DB32-6 phage clones (7 aa) | |
|---|---|
| 7P32-1, 4, 5, 7, 8, 9, 10, 11, 12, 13, 16, 17, 19, 20 (SEQ ID NO:28) | T H K E Y H W |
| 7P32-3, 6 (SEQ ID NO:29) | S H K E W H V |
| 7P32-15 (SEQ ID NO:30) | M H K E W H L |

| DB25-2 phage clones (12 aa) | Peptide Sequences |
|---|---|
| PC25-8 (SEQ ID NO:31) | V P Q L G W W Y D E P T |
| PC25-14 (SEQ ID NO:32) | T F H W S P W P W L D E |
| PC25-2-1 (SEQ ID NO:33) | N A L Y M I R L S S E L |
| PC25-26 (SEQ ID NO:34) | Y S S E W Y T V P L P L |
| PC25-2-17 (SEQ ID NO: ) | S H R W V E W R N F F P |

US 8,637,035 B2

ANTI-DENGUE VIRUS ANTIBODIES

CROSS REFERENCE TO RELATED APPLICATION

This application claims priority to U.S. Provisional Application No. 61/364,845, filed on Jul. 16, 2010, the content of which is incorporated herein by reference in its entirety.

BACKGROUND OF THE INVENTION

Dengue, caused by dengue virus infection, is the most important arthropod-borne viral disease in humans that causes an expanding public health problem in tropical and subtropical regions of the world. There were approximately 50-100 million cases of dengue fever (DF) and 500,000 cases of dengue hemorrhagic fever (DHF) per year, with 2.5 billion people at risk for infection worldwide (Farrar et al., 2007; Halstead, 2007; Normile, 2007). Dengue infection can cause fever, headache and joint pain, leading to mild DHF. It can also cause DHF/dengue shock syndrome (DSS), which is life-threatening (Kalayanarooj et al., 1997).

Dengue virus (DENV) has four genetically and antigenically related viral serotypes, DENV-1, -2, -3, and -4. DENV is positive-sense single-stranded RNA of approximately 11 kb genome of the genus Flavivirus, family Flaviviridae. Flaviviruses encodes a single polyprotein that is processed by host and viral protease to produce three structural proteins, i.e., capsid (C) protein, precursor membrane/membrane (prM/M) and envelope (E) protein, and seven nonstructural proteins (NS1, NS2A, NS2B, NS3, NS4A, NS4B and NS5) (Rice et al., 1985). The C is an 11 kDa small protein, highly positively charged, that is required for the assembly of nucleocapsid and maturation of viral particles (Kuhn et al., 2002). The NS1 is a 45 kDa glycoprotein that is translocated into the lumen of the ER and secreted from the cell (Schlesinger et al., 1990). It is involved in functions within the viral RNA replication complex (Lindenbach and Rice, 1997, 1999). NS1 protein forms stable oligomers (dimers and hexamers) in solution (Flamand et al., 1999; Winkler et al., 1989). The E protein is a 53 kDa glycoprotein and important for viral entry, its cellular receptor binding capabilities and to the induction of neutralizing antibodies (Kuhn et al., 2002; Pierson et al., 2008; Pokidysheva et al., 2006; Roehrig, 2003). E protein is the external surface of DENY and consists of 90 E protein dimers (Kuhn et al., 2002; Zhang et al., 2003).

The E protein monomer contains three structural and functional domains (Crill and Roehrig, 2001; Modis et al., 2003, 2005; Rey et al., 1995; Roehrig, 2003). E protein domain I (E-DI) is a central n-barrel structure. E protein domain II (E-DII) is organized into two long finger-like structures and contains the flavivirus conserved fusion loop. E protein domain III (E-DIII) adopts an immunoglobulin-like fold and has been suggested to mediate interactions between the virus and the receptor on host cell (Mukhopadhyay et al., 2005). The biological characteristics and epitopes specificity of mouse MAbs have revealed the antigenic structure of flavivirus E. Antibodies that recognize epitopes involving in E-DI are both virus-specific and cross-reactive, predominately non-neutralizing epitopes. Antibodies reactive to E-DII are broadly cross-reactive, but weakly to non-neutralizing. E-DIII elicits serotype-specific, highly protective neutralizing antibodies and cross-reactive antibodies (Crill and Chang, 2004; Crill and Roehrig, 2001; Gromowski et al., 2008; Roehrig et al., 1998; Sukupolyi-Petty et al., 2007).

Antibodies play an important role in protection against DENY. However, antibodies have also been implicated in the development of sever clinical manifestations of DENV infection. Antibody-dependent enhancement (ADE) describes an increase in the efficiency of virus infection in the presence of non-neutralizing or sub-neutralizing concentrations of cross-reactive anti-E immunoglobulins (Halstead and O'Rourke, 1977). The Ab-virus complex attaches to the Fc receptors on circulating monocytes, thereby DENV has been shown to replicate to higher titers in Fc receptor-bearing cells (Halstead, 1988; Littaua et al., 1990). The overall outcomes lead to the potential for more severe disease. Moreover, anti-NS1 antibodies have been reported to confer protection against DENV infection (Falgout et al., 1990; Qu et al., 1993). In addition, it was shown that anti-NS1 antibodies can bind to endothelial cells and cross-react with some self-antigens, induce the expression of cytokines, chemokines, and cause apoptosis (Lin et al., 2005; Lin et al., 2002). These studies suggested that antibodies to E and NS1 proteins are also involved in the pathogenesis of DENV disease. Hence, there is a need for a safe and effective vaccine to DENV.

SUMMARY OF THE INVENTION

In one aspect, the present invention features a number of anti-dengue virus monoclonal antibodies, i.e., DB2-3, DB3-4, DB5-2, DB6-1, DB7-3, DB8-1, DB9-1, DB11-3, DB12-3, DB13-19, DB16-1, DB19-4, DB20-6, DB21-6, DB22-4, DB23-3, DB24-2, DB25-2, DB27-3, DB28-4, DB29-1, DB31-4, DB32-6, DB33-3, DB34-1, DB36-2, DB37-1, DB38-1, DB39-2, DB40-2, DB41-2, and DB42-3, as well as antigen-binding fragments (e.g., $F(ab')_2$, Fab, or Fv) and functional variants thereof (e.g., humanized antibodies, chimeric antibodies, or single-chain antibodies). In one example, a functional variant of one of the above-listed monoclonal antibodies contains (i) a heavy chain variable region ($V_H$) including all of the complementarity determining regions (CDRs) in that of the monoclonal antibody, and (ii) a light chain variable region ($V_L$) including all of the CDRs in that of the monoclonal antibody. In another example, a functional variant contains the same $V_H$ and $V_L$ as a monoclonal antibody.

In a second aspect, this invention features a method for treating dengue virus infection by administering to a subject in need thereof an effective amount of any of the anti-dengue virus antibodies described above. The term "treating" as used herein refers to the application or administration of a composition including one or more active agents to a subject who suffers from dengue virus infection, a symptom of the dengue virus infection, or is at risk for dengue virus infection, with the purpose to cure, heal, alleviate, relieve, alter, remedy, ameliorate, improve, or affect the infection, the symptoms of the infection, or the predisposition toward the infection. "An effective amount" as used herein refers to the amount of each active agent required to confer therapeutic effect on the subject, either alone or in combination with one or more other active agents. Effective amounts vary, as recognized by those skilled in the art, depending on route of administration, excipient choice, and co-usage with other active agents.

In a further aspect, the invention features a method for detecting presence of a dengue virus antigen in a sample. The sample can be a serum sample from a human patient suspected of having dengue virus infection. It also can be a cell culture sample. This method includes at least the following steps: providing a sample suspected of containing a dengue virus antigen, contacting the sample with any of the anti-dengue virus antibodies described above, and determining whether the antibody binds to an antigen in the sample. Binding of the antibody to the antigen indicates presence of a dengue virus antigen in the sample, Also within the scope of this invention are (i) a pharmaceutical composition for treating dengue virus infection, the pharmaceutical composition containing one or more of the above-mentioned anti-dengue virus antibodies, and (ii) the use of any of these anti-dengue virus antibodies in manufacturing a medicament for the treatment of dengue virus infection.

The details of one or more embodiments of the invention are set forth in the description below. Other features or advantages of the present invention will be apparent from the following drawings and detailed description of an example, and also from the appended claims.

BRIEF DESCRIPTION OF THE DRAWINGS

The drawings are first described.

FIG. 1 is a diagram showing the amino acid sequences of the (A) $V_H$ and (B) $V_L$ regions of DB2-3, DB13-19, DB23-3, DB25-2, DB32-6, ad DB42-3.

FIG. 2 is a diagram showing alignments of phage-displayed peptide sequences selected by DB32-6 and DB25-2. Consensus motifs are indicated by boldface type.

DETAILED DESCRIPTION OF THE INVENTION

Described herein are isolated anti-dengue virus antibodies, including the monoclonal antibodies listed in Table 1 below, i.e., DB2-3, DB3-4, DB5-2, DB6-1, DB7-3, DB8-1, DB9-1, DB11-3, DB12-3, DB13-19, DB16-1, DB19-4, DB20-6, DB21-6, DB22-4, DB23-3, DB24-2, DB25-2, DB27-3, DB28-4, DB29-1, DB31-4, DB32-6, DB33-3, DB34-1, DB36-2, DB37-1, DB38-1, DB39-2, DB40-2, DB41-2, and DB42-3, as well as their antigen-binging fragments and genetically engineered functional variants.

The term "isolated antibody" used herein refers to an antibody substantially free from naturally associated molecules, i.e., the naturally associated molecules constituting at most 20% by dry weight of a preparation containing the antibody. Purity can be measured by any appropriate method, e.g., column chromatography, polyacrylamide gel electrophoresis, and HPLC.

Any of the monoclonal antibodies listed in Table 1 can be prepared by conventional methods, e.g., hybridoma technology, recombinant technology, or chemical synthesis. See, e.g., Harlow and Lane, (1988) Antibodies: A Laboratory Manual, Cold Spring Harbor Laboratory, New York; and the example below.

Antigen-binding fragments (e.g., F(ab')$_2$, Fab, or Fv) of a monoclonal antibody can be generated by known techniques. For example, F(ab')$_2$ fragments can be produced by pepsin digestion of an antibody molecule and Fab fragments can be generated by reducing the disulfide bridges of F(ab')$_2$ fragments.

A functional variant of a monoclonal antibody refers to an antibody that contains the same antigen-binding residues (e.g., the specific-determining residues in the CDRs; see Almagro, J. Mol. Recognit. 17:132-143; 2004) of the monoclonal antibody, and thus, the same antigen specificity. A functional variant can include a $V_H$ at least 70% (e.g., 75%, 80%, 85%, 90%, or 95%) identical to that of its parent monoclonal antibody and a $V_L$ at least 70% (e.g., 75%, 80%, 85%, 90%, or 95%) identical to that of the monoclonal antibody. Alternatively, a functional variant can include a $V_H$ containing CDRs each of which share at least 80% (e.g., 85%, 90%, or 95%) sequence identify to the corresponding CDR in the monoclonal antibody and a $V_L$ containing CDRs each of which share at least 80% (e.g., 85%, 90%, or 95%) sequence identify to the corresponding CDR in the monoclonal antibody. In one example, the functional variant contains the same $V_H$ and $V_L$ as the parent monoclonal antibody. CDRs and the specific-determining residues in them can be determined based on the amino acid sequences of its $V_H$ and $V_L$. See world wide web at bioinf.org.uk/abs and Almagro, J. Mol. Recognit. 17:132-143; 2004. The binding-specificity of a functional variant described herein can be examined using methods known in the art, e.g., ELISA or western-blot analysis.

For example, an isolated antibody can include the amino acid sequence of the $V_H$ region of DB32-6 (SEQ ID NO:1) and the amino acid sequence of the $V_L$ region of DB32-6 (SEQ ID NO:5). In another example, an isolated antibody can contain the heavy chain CDR1, CDR2, and CDR3 sequences of DB32-6 (SEQ ID NOs: 2, 3, and 4, respectively), and the light chain CDR1, CDR2, and CDR3 sequences of DB32-6 (SEQ ID NOs: 6, 7 and 8, respectively).

As used herein, "percent homology" of two amino acid sequences is determined using the algorism described in Karlin and Altschul, Proc, Natl. Acad. Sci. USA 87:2264-2268, 1990, modified as described in Karlin and Altschul, Proc, Natl. Acad. Sci. USA 5873-5877, 1993. Such an algorism is incorporated into the NBLAST and XBLAST programs of Altschul et al., J. Mol. Biol. 215:403-410, 1990. BLAST protein searches are performed with the XBLAST program, score=50, wordlength=3, to obtain amino acid sequences homologous to a reference polypeptide. To obtain gapped alignments for comparison purposes, Gapped BLAST is utilized as described in Altschul et al., Nucleic Acids Res. 25:3389-3402, 1997. When utilizing the BLAST and Gapped BLAST programs, the default parameters of the respective programs (e.g., XBLAST and NBLAST) are used. See world wide web at ncbi.nlm.nih.gov.

The functional variant mentioned above can be a humanized antibody, a chimeric antibody, a single-chain antibody, or a domain antibody (dAb; see Ward, et. Al., 1989, Nature, 341:544-546) derived from one of the monoclonal antibodies listed in Table 1 below.

A humanized antibody contains a human immunoglobulin (i.e., recipient antibody) in which regions/residues responsible for antigen binding (i.e., the CDRs, particularly the specific-determining residues therein) are replaced with those from a non-human immunoglobulin (i.e., donor antibody). In some instances, one or more residues inside a frame region of the recipient antibody are also replaced with those from the donor antibody. A humanized antibody may also contain residues from neither the recipient antibody nor the donor antibody. These residues are included to further refine and optimize antibody performance. Antibodies can also be humanized by methods known in the art, e.g., recombinant technology.

A chimeric antibody is a molecule in which different portions are derived from different animal species, such as those having a variable region derived from a murine monoclonal antibody and a human immunoglobulin constant region. Such an antibody can be prepared via routine techniques described in, e.g., Morrison et al. (1984) Proc. Natl. Acad. Sci. USA 81, 6851; Neuberger et al. (1984) Nature 312, 604; and Takeda et al. (1984) Nature 314:452.

A single-chain antibody can be prepared via recombinant technology by linking a nucleotide sequence coding for a $V_H$ chain and a nucleotide sequence coding for a $V_L$ chain. Preferably, a flexible linker is incorporated between the two variable regions.

Any of the anti-dengue virus antibody described herein can be used for treating dengue virus infection. To perform this treatment, an anti-dengue virus antibody can be mixed with a pharmaceutically acceptable carrier, either alone or in combination with an anti-viral agent, to form a pharmaceutical composition. "Acceptable" means that the carrier must be compatible with the active ingredient of the composition (and preferably, capable of stabilizing the active ingredient) and not deleterious to the subject to be treated. Suitable carriers include microcrystalline cellulose, mannitol, glucose, defatted milk powder, polyvinylpyrrolidone, and starch, or a combination thereof.

The above-described pharmaceutical composition can be administered to a subject in need of the treatment (i.e., a human patient who suffers from or is at risk for dengue virus infection) via a conventional route, e.g., orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

In addition, the pharmaceutical composition described above can be administered to the subject via injectable depot routes of administration such as using 1-, 3-, or 6-month depot injectable or biodegradable materials and methods.

The anti-dengue virus antibodies described herein can also be used as a diagnostic agent for determining whether a subject is infected with dengue virus via a conventional method, e.g., ELISA or Westernblot.

Without further elaboration, it is believed that one skilled in the art can, based on the above description, utilize the present invention to its fullest extent. The following specific example is, therefore, to be construed as merely illustrative, and not limitative of the remainder of the disclosure in any way whatsoever. All publications cited herein are incorporated by reference.

Generation and Characterization of Monoclonal Antibodies Against Dengue Virus Type 2

(1) Materials and Methods

BHK-21 cells were grown at 37° C. with 5% $CO_2$ in Minimal Essential Medium (MEM, Gibco-BRL, Grand Island, N.Y.) supplemented with 10% heat-inactivated fetal bovine serum (FBS, Gibco), and 100 U/ml penicillin, 100 µg/ml streptomycin, 0.25 µg/ml amphotericin B (Antibiotic-Antimycotic, Gibco). *Aedes albopictus* C6/36 cells were grown at 28° C. in Mitsuhashi and Maramorosch (MM) insect medium (Sigma-Aldrich, St. Louis, Mo.)/Dulbecco's modified Eagle's medium (DMEM, Gibco) containing 10% heat-inactivated fetal bovine serum and 100 U/ml penicillin, 100 µg/ml streptomycin, 0.25 amphotericin B (Antibiotic-Antimycotic, Gibco). The four DENVs, DENV-1 Hawaii, DENV-2 New Guinea C and 16681, DENV-3 H87, and DENV-4 H241, were provided by Dr. Duane J. Gubler from the Centers for Disease Control and Prevention, Fort Collins, U.S.A. These viruses were passaged in C6/36 cells.

Patients infected with DENV-2 were recruited from an outbreak in Kaohsiung, a metropolitan city in southern Taiwan, in 2002 as described previously (Wang et al., 2006). An active physician-based dengue surveillance system has been established in the local hospitals and National Taiwan University Hospital (NTUH) in northern Taiwan. DHF and DF were diagnosed according to the WHO case definitions (WHO, 1997). With informed consent, acute (days 1 to 7 after onset) and convalescent-phase (between day 87 and 4 months after onset) blood samples were collected. All the samples were centrifuged at 800×g for 10 min at 4° C. and stored at −80° C. until use. Serum and plasma samples were tested by at least two of the following four methods: (i) serotype-specific reverse transcriptase-polymerase chain reaction (RT-PCR) test at acute phase, (ii) virus isolation in mosquito C6/36 cells, (iii) dengue-specific IgM, and (iv) a hemagluttination-inhibition test for a fourfold increase in titers of antibody to DENV in convalescent-phase serum samples (Lanciotti et al., 1992). Normal serum samples from healthy adults who tested negative for anti-DENV antibodies by commercial capture ELISA kits (PanBio, Queensland, Australia) (Vaughn et al., 1998; Vaughn et al., 1999) were used as references to establish cutoff values.

Anti-DENV-2 MAbs were generated according to previously described procedures (Wu et al., 2003). Female, 4- to 6-week-old, BALB/c mice were immunized with purified DENV-2 as antigen. Following four inoculations with virus, serum was harvested and tested for the immunoreactivity against DENV-2. The most suitable mouse was selected for administration of the final boost. The splenocytes from the immunized mouse spleen were fused with mouse myeloma NS-1 cells in the presence of 50% (v/v) polyethylene glycol-1500 (PEG-1500, Roche Molecular Biochemicals, Indianapolis, Ind.). The mixture was diluted by 10 ml serum-free DMEM then centrifuged at 400 g for 5 min. Fused cells were culture in DMEM supplemented with 15% FBS, HAT medium and hybridoma cloning factor (Roche) in 96-well tissue culture plates. About 2 weeks after fusion, culture supernatants were screened by ELISA for MAbs that bound DENV-2-infected C6/36 cells, but not uninfected cells, were regarded as positive clones. Selected clones were subcloned by limiting dilutions. Hybridoma clones were isotyped using a commercially isotyping kit (Southern Biotech, Birmingham, Ala.) by ELISA. Ascites fluids were produced in pristine-primed BALB/c mice. MAbs were affinity-purified by standard protein G-Sepharose 4B gel (Amershan Pharmacia Biotech, Piscataway, N.J.) according to the manufacturer's instructions.

C6/36 cells monolayer in 96-well plates were infected with DENV-1 to −4 (DENY-1 Hawaii, DENV-2 16681, DENV-3 H87, and DENV-4 H241) at a multiplicity of infection (MOI) of 0.5. One µg/ml MAbs in PBS supplemented with 1% (w/v) BSA (Sigma-Aldrich, St. Louis, Mo.) were added to the plates in triplicate and incubated at room temperature for 1 h followed by three times washes with PBS containing 0.1% (v/v) Tween-20 (PBST$_{0.1}$). Horseradish peroxidase (HRP)-conjugated anti-mouse IgG (Jackson ImmunoResearch Laboratories, West Grove, Pa.) diluted 1:2,000 in PBS supplemented with 1% (w/v) BSA was then added at room temperature for 1 h follow by five times wash steps. The plates were incubated with peroxidase substrate o-phenylenediamine dihydrochloride (OPD; Sigma) and stopped with 3 N HCl. Optical density was measured by a microplate reader at 490 nm.

BHK-21 cells were fixed with 1:1 methanol/acetone for 10 min at −20° C. Cells were then incubated in block solution (PBS supplemented with 1% BSA) for 1 h at room temperature. Primary antibody targeting the dengue virus (DB MAbs) or control antibodies (normal mouse IgG, Jackson ImmunoResearch Laboratories) diluted 1:250 in block solution were then added for 1 h at room temperature followed by three times washes with PBS supplemented with 0.1% Tween-20. Secondary antibody, FITC-conjugated goat anti-mouse IgG (Jackson ImmunoResearch Laboratories) diluted 1:250 supplemented with DAPI (Invitrogen, Carlsbad, Calif.) diluted 1:2,000 in block solution were then added for 1 h at room temperature followed by washes with PBS supplemented with 0.1% Tween-20. The binding activity of DB monoclonal antibodies or control antibodies to BHK-21 infected with DENV-2 or mock were observed and photographed with a fluorescence microscope.

An expression construct of DENV-2 (PL046) E was obtained from Dr. Y.-L. Lin (Yu et al., 2006) and prepared to express E-DI-II and E-DIII. A DNA fragment corresponding to E-DI-II was PCR amplified with the following primer, forward: 5'-GATGCTAGCATGCGTTGCATAG GAATA-3' (NheI site is underlined; SEQ ID NO:9) and reverse: 5'-GAT CTCGAGTCCTTTGAGCTG TAGTTT-3' (Xho site is underlined; SEQ ID NO:10). Appropriate primers were also designed for constructing E-DIII, forward: 5'-GAT GCTAGCATGAAAGGAATGTCATAC-3' (NheI site is underlined; SEQ ID NO:11) and reverse: 5'-GAT CTCGAGTTGGCCGATAGAACT-3' (Xho site is underlined; SEQ ID NO:12). The primers were designed for cloning into the pET21a vector (Merck, Darmstadt, Germany). The recombinant E-DI-II, comprising amino acids 1-295 of the E protein was tagged to flag and hexahistidine at the C terminus for affinity purification. The recombinant E-DIII, comprising amino acids 295-400 of the E protein was tagged to flag and hexahistidine, too. The expression plasmids were transformed into *Escherichia coli* strain BL21 (DE3). Twenty ml culture of bacteria was grown in LB medium containing 50 µg/ml ampicillin to an OD600 of approximately 0.6 and induced with 1 mM isopropyl-β-D-thiogalactopyranoside (IPTG) at 37° C. for 4 h. The bacterial pellets were harvested and sonicated. The recombinant proteins, E-DI-II and E-DIII, were analyzed by 12% SDS-PAGE and stained with coomassie blue or for Western blot analysis.

The cells were harvested after viral infection and lysed with RIPA buffer (10 mM Tris, pH 7.5, 150 mM NaCl, 5 mM EDTA, 0.1% sodium dodecyl sulfate [SDS], 1% Triton X-100, 1% sodium deoxycholate and proteinase inhibitor cocktail tablet, Roche). Cell lysates or expression proteins were centrifuged at 12,000 g for 20 min at 4° C. and collected the supernatants. Equal amounts of total cell extracts were mixed with sample buffer (Bio-Rad Laboratories, Richmond, Calif.). Protein samples were separated by SDS-PAGE, followed by transfer to nitrocellulose membrane (Hybond-C Super; Amersham, Little Chalfont, UK). The non-specific antibody binding sites were blocked with 5% skimmed milk (Becton Dickinson and Co., Franklin Lakes, N.Y.) in PBS and incubated with primary, DB MAbs, (ascites at 1:250 to 1:5, 000 dilutions) and secondary antibodies, HRP-conjugated anti-mouse IgG (Jackson ImmunoResearch Laboratories) at 1:10,000 dilution each at room temperature for 1 h. The signals were detected by enhanced chemiluminescence reagents (ECL, Thermo Fisher Scientific, San Jose, Calif.).

ELISA plates were coated with 50 µl/well of capture MAbs (DB42-3 recognized E protein) at a concentration of 0.5 µg/ml in 0.1 M sodium bicarbonate buffer (pH 8.6) and were incubated at 4° C. for 6 h. After being twice washed with PBS, the plates were blocked with PBS supplemented with 1% BSA at 4° C. overnight, and then were three times washes with PBS supplemented with 0.1% Tween-20. The plates were incubated with diluted virus-infected culture supernatants, 5×10$^6$ plaque forming unit (PFU)/ml at room temperature for 1 h followed by three times washes with PBS supplemented with 0.1% Tween-20. Serum samples at 1:100, 1:400, 1:1,600, and 1:3, 200 dilutions of DENV-2-infected patients or normal human sera (NHS) were added to plates and incubated at room temperature for 1 h. After three times washes, horseradish peroxidase (HRP)-conjugated anti-human IgG or IgM (Jackson ImmunoResearch Laboratories, West Grove, Pa.) diluted 1:10,000 was then added at room temperature for 1 h follow by five times wash steps. The plates were incubated with OPD (Sigma) and terminated with 3 N HCl. Optical density was measured by a microplate reader at 490 nm.

Eight 3-fold serial dilutions of MAbs (200 µg/ml to 0.09 µg/ml) were mixed with an equal volume of 200 PFU of DENV-2 and incubated at 4° C. for 1 h. The final concentrations of MAbs at the PRNT ranged from 100 to 0.05 µg/ml. The 100 µl of antibody-virus mixture was added to a monolayer of BHK-21 cells in a 12-well plate in duplicate. After absorption of virus for 2 h, supernatant was removed and 2 ml of 1% (w/v) carboxyl methyl cellulose (Sigma) in MEM plus 2% (v/v) FBS was layered onto the infected cells. After incubation at 37° C. for 5 to 7 days, viral plaques that formed on the cell monolayer were fixed by 1 ml 3.7% formaldehyde (Sigma) at RT for 1 h. The cells were stained with 1% crystal violet to visualize the plaques. Percentage of plaque reduction was calculated as: % Inhibition=100-[(plaque number incubated with MAb/plaque number without MAb)×100].

Breeder mice of the ICR strain were purchased from the animal center, National Taiwan University. Purified MAbs at dose of 10 µg/ml were incubated with 1×10$^4$ PFU (25-fold LD$_{50}$) of DENV-2 at 4° C. for 30 mins. Twenty microliter of the reaction mixture was then inoculated to two-day-old suckling mouse brain by intracranial (i.c.) injection. Survival rate and signs of illness including paralysis were observed daily for 21 days following challenge. Animal care was carried out in accordance with the guidelines of Academia Sinica (Taipei, Taiwan).

In postexposure therapeutic experiments, mice were passively transferred 5 µg of MAb by an i.c. route after 1 day of infection. The hemorrhage mouse model has been described previously (Chen H C et al., 2007; and Yen et al., 2008). C57BL/6 mice were originally purchased from Jackson Laboratory (Bar Harbor, Me.) and bred at the Laboratory Animal Center National Taiwan University College of Medicine. All mice were housed in pathogen-free barrier facilities and infected at 4 to 5 weeks of age. Before inoculation, MAbs at 100 µg/ml or PBS were incubated with 2×10$^8$ pfu of DENV-2 (16681) at 4° C. for 30 mins. The 100 µl mixture was inoculated intradermally at four sites on the upper back. At day 3 after inoculation, mice were killed for the observation of hemorrhage development.

Total RNA was extracted from approximately 1×10$^7$ hybridoma cells using the TRIzol reagent (Invitrogen) and mRNA was isolated with the NucleoTrap mRNA Mini Kit (Macherey-Nagel GmbH & Co. KG.). Purified mRNA was reverse transcribed by using oligo (dT) as a primer with the ThermoScript RT-PCR system (Invitrogen). The variable heavy- and light-chain domains ($V_H$ and $V_L$) were amplified from the cDNA product by PCR with a variety of primer sets (Dubel et al., 1994; Orlandi et al., 1989; Orum et al., 1993). A 30 cycles PCR at 95° C. for 30 s, 55° C. for 30 s, and 68° C. for 60 s was performed with pfu turbo DNA polymerase (Merck). The PCR products were extracted and inserted into the plasmid pGEM-T Easy using the TA kit (Promega, Madison, Wis.). We then subjected the resulting plasmid to DNA sequencing to determine the $V_H$ and $V_L$ sequences of neutralizing MAbs. Software Vector NTI (InforMax) was used for sequences analysis. From these sequences the framework regions (FR) and complementarity-determining regions (CDR) were analyzed by comparison to Kabat database and by alignment to ImMunoGeneTics database (Lefranc et al., 2009).

Phage display biopanning procedures were performed according to previously reports Briefly, an ELISA plate was coated with MAbs at 100 ng/ml. Samples of 100 µl diluted MAb were then added to wells and incubated at 4° C. for 6 h. After washing and blocking, the phage-displayed peptide library (New England BioLabs, Inc.) was diluted to $4 \times 10^{10}$ pfu of phage and incubated for 50 mins at RT. After washing, bound phage was eluted with 100 µl 0.2 M glycine/HCl (pH2.2) and neutralized with 15 µl 1M Tris/HCl (pH9.1). The eluted phage was amplified in ER2738 for subsequent rounds of selection. The phage was titrated onto LB medium plates containing IPTG and X-Gal. The biopanning protocol for the second and third rounds was identical to the first round, with the addition of $2 \times 10^{11}$ pfu of phage for biopanning. An ELISA plate was coated with 50 µl MAbs 50 µg/ml. After washing and blocking, amplified phage diluted 5-fold was added to coated plate and incubated at RT for 1 h. After washing, 1:5000 diluted HRP-conjugated anti-M13 antibody (GE Healthcare) was added at RT for 1 h. OPD developed and was terminated with HCl. Optical density was measured at 490 nm.

We used the recombinant expression plasmid pCBD2-2J-2-9-1 to generate virus-like particle (VLP) mutants. Various VLP mutants were generated by site-directed mutagenesis derived from pCBD2-2J-2-9-1 as a template. PCR was performed using pfu ultra DNA polymerase (MERCK) and all mutant constructs were confirmed by sequencing. BHK-21 cells were transfected with plasmids of various VLPs. After two days transfection, the cells were washed with PBS supplemented with 1% FBS, fixed with 3.7% formaldehyde, and permeabilized in PBS supplemented with 1% FBS, 0.1% saponin (Sigma-Aldrich) at 4° C. for 10 min. For staining, cells were incubated with MAbs at 4° C. for 30 min, DB32-6, DB25-2, 3H5, and mix MAbs (4G2, DB2-3, DB13-19, DB21-6, and DB42-3) at a concentration of 0.1, 1, 1, and 1 µg/ml, respectively. After being washed twice, R-Phycoerythrin (PE)-conjugated AffiniPure F(ab')$_2$ fragment goat anti-mouse IgG (H+L) (Jackson ImmunoResearch Laboratories, West Grove, Pa.) diluted to 1:250 was then added at 4° C. for 30 min and analyzed by flow cytometry. Reactive recognition was performed according to previously described procedures.

Construction and expression of humanized DB32-6 were carried out. Two human genes, GenBank accession DI084180 and DI075739, were similar to DB32-6 $V_H$ and $V_L$, being 94.7% and 92.2% identical, respectively. Humanized DB32-6 $V_H$ consisted of the modified FR1 to FR4 from the accession DI084180 gene, and the CDR1 to CDR3 of the DB32-6 $V_H$, respectively. The humanized DB32-6 $V_L$ consisted of the modified FRs from the accession DI075739 gene and the CDRs of the DB32-6 $V_L$. The humanized DB32-6 $V_H$ and $V_L$ were synthesized (GENEART, Germany) and amplified by PCR using pfu Turbo (EMD Bioscience). The resulting $V_H$ was cloned into modified expression vector peDNA3.1 (Invitrogen) with a signal peptide and human IgG1 constant region. The $V_L$ was cloned into modified expression vector pSecTag (Invitrogen). The $V_H$ and $V_L$ plasmids were cotransfected into CHO-K$^1$ cells and selected by G 418 and puromycin for 2-3 weeks. Transformed cells were limit diluted in 96-well plates. After two weeks, stable clones produced humanized antibody in the McCoy's 5A medium (Sigma-Aldrich), and were identified by ELISA. Humanized antibodies were produced by CELLine AD 1000 (INTEGRA Biosciences, Switzerland), according to manufacturer's recommendations.

Murine and humanized DB32-6 MAbs affinity analysis for E-DIII of DENV-2 was is performed by surface plasmon resonance (BIAcore X, Biacore, Inc). Purified E-DIII (50 µg/ml) was immobilized on a CM5 sensor chip (Biacore, Inc) and injected at a flow rate of 10 µl/min. The MAbs were diluted to 4, 2, 1, 0.5, 0.25, and 0 nM in HBS-EP buffer (Biacore, Inc). MAbs were injected at a flow rate of 30 µl/min for 3 min and then allowed to dissociate over 1.5 min. Regeneration of the surface was achieved with an injection of 10 mM glycine HCl, 0.2 M NaCl (pH3.0) before each MAb injection. The data were analyzed by the BIAevaluation software with a global fit 1:1 binding model.

(2) Generation and Identification of MAbs Against DENV-2

A total of 32 MAbs against DENV-2, listed in Table 1 below, were generated after immunization of mice with DENV-2 strain 16681.

TABLE 1

Characterization of DENV-2 MAbs by IFA, ELISA, WB and PRNT$_{50}$ (µg/ml)

| MAbs | Isotype, Light chain | Specificity | IFA D2 | ELISA D1 | ELISA D2 | ELISA D3 | ELISA D4 | WB D1 | WB D2 | WB D3 | WB D4 | PRNT$_{50}$ (µg/ml) D2 |
|---|---|---|---|---|---|---|---|---|---|---|---|---|
| DB2-3 | IgG1, κ | E-DI-II | + | − | + | − | − | − | + | − | − | ≤1.2 |
| DB3-4 | IgG1, κ | E | + | − | + | − | − | − | + | − | − | ≤3.7 |
| DB5-2 | IgG1, κ | C | + | − | + | − | − | − | − | − | − | n.d. |
| DB6-1 | IgG2a, κ | NS1 | + | − | + | − | − | − | + | − | − | n.d. |
| DB7-3 | IgG1, κ | C | + | − | + | − | − | − | + | − | − | n.d. |
| DB8-1 | IgM, κ | n.d. | n.d. | n.d | n.d | n.d | n.d | n.d | n.d | n.d | n.d | n.d. |
| DB9-1 | IgG1, κ | E-DI-II | + | − | + | − | − | − | + | − | − | ≤3.7 |
| DB11-3 | IgG1, κ | C | + | − | + | − | − | − | − | − | − | n.d. |
| DB12-3 | IgG1, κ | NS1 | + | − | + | − | − | − | + | − | − | n.d. |
| DB13-19 | IgG1, κ | E-DI-II | + | + | + | + | + | + | + | + | + | ≤33 |
| DB16-1 | IgG2a, κ | NS1 | + | + | + | + | + | + | + | + | + | n.d. |

TABLE 1-continued

Characterization of DENV-2 MAbs by IFA, ELISA, WB and PRNT$_{50}$ (μg/ml)

| MAbs | Isotype, Light chain | Specificity | IFA D2 | ELISA D1 | D2 | D3 | D4 | WB D1 | D2 | D3 | D4 | PRNT$_{50}$ (μg/ml) D2 |
|---|---|---|---|---|---|---|---|---|---|---|---|---|
| DB19-4 | IgG2b, κ | E | + | − | + | − | − | − | + | − | − | ≤3.7 |
| DB20-6 | IgG1, κ | NS1 | + | + | + | + | + | + | + | + | + | n.d. |
| DB21-6 | IgG1, κ | E-DI-II | + | + | + | + | + | − | − | − | − | >33 |
| DB22-4 | IgG2a, κ | E-DI-II | + | − | + | − | − | − | − | − | − | >33 |
| DB23-3 | IgG2a, κ | E-DI-II | + | − | + | − | − | − | + | − | − | ≤0.41 |
| DB24-2 | IgG2a, κ | E | + | − | + | − | − | − | + | − | − | ≤3.7 |
| DB25-2 | IgG1, κ | E-DIII | + | − | + | − | − | − | + | − | − | ≤1.2 |
| DB27-3 | IgG1, κ | E-DI-II | + | − | + | − | − | − | + | − | − | >33 |
| DB28-4 | IgG1, κ | C | + | + | + | − | − | n.d | + | n.d | n.d | n.d. |
| DB29-1 | IgG1, κ | NS1 | + | + | + | + | + | + | + | + | + | n.d. |
| DB31-4 | IgG1, κ | C | + | + | + | − | − | n.d | + | n.d | n.d | n.d. |
| DB32-6 | IgG2b, κ | E-DIII | + | − | + | − | − | − | + | − | − | ≤0.14 |
| DB33-3 | IgG1, κ | E-DI-II | + | + | + | + | + | + | + | + | + | >33 |
| DB34-1 | IgM, κ | n.d. | n.d. | n.d | n.d | n.d | n.d | n.d | n.d | n.d | n.d | n.d. |
| DB36-2 | IgG1, κ | E | + | − | + | − | − | − | − | − | − | n.d. |
| DB37-1 | IgG1, κ | E | + | − | + | − | + | − | + | − | + | >33 |
| DB38-1 | IgG1, κ | NS1 | + | − | + | − | − | − | + | − | − | n.d. |
| DB39-2 | IgG1, κ | E-DI-II | + | + | + | + | + | + | + | + | + | >33 |
| DB40-2 | IgM, κ | n.d. | n.d. | n.d | n.d | n.d | n.d | n.d | n.d | n.d | n.d | n.d. |
| DB41-2 | IgG1, κ | NS1 | + | − | + | + | + | − | + | − | + | n.d. |
| DB42-3 | IgG1, λ | E-DI-II | + | + | + | + | + | + | + | + | + | ≤3.7 |
| 3H5 | IgG1 | E-DIII | + | − | + | − | − | − | + | − | − | ≤0.41 |
| 4G2 | IgG2a | E-DI-II | + | + | + | + | + | + | + | + | + | ≤11 |

MAbs, monoclonal antibodies; IFA, immunofluorescence assay; ELISA, enzyme-linked immunosorbent assay; WB, Western blotting; PRNT, plaque reduction neutralization test. Ig, immunoglobulin; E, envelope protein; E-DI-II, envelope protein domain I-II; E-DIII, envelope protein domain III; NS1, nonstructural protein 1; C, capsid protein. (+) positive result to DENV, A$_{490}$ > 0.2; (−) negative result to DENV, A$_{490}$ < 0.2. n.d. not determined.

The immunoglobulin (Ig) isotype determinations revealed that the 32 MAbs were comprised of 22 IgG1, 5 IgG2a, 2 IgG2b, and 3 IgM (Table 1). 29 of the IgG MAbs that reacted with DENV-2-infected cells and did not react with mock-infected cells were identified using immunofluorescence assay and ELISA (Table 1). ELISA and Western blotting were used to test the specificities of MAbs for the four DENVs (DENV-1 Hawaii, DENV-2 16681, DENV-3 1187, and DENV-4 11241) (Table 1). Based on Western blot analysis using a nonreducing condition, 17 of the MAbs recognized E protein (53 kDa), 7 recognized dimeric NS1 protein (75 kDa), and 2 recognized C protein (11 kDa). Six MAbs could not be identified by Western blotting. In order to identify the target proteins of these MAbs, we prepared BHK-21 cells transfected with plasmids expressing DENV-2 C, prM, prM-E, E, NS1, NS2A, NS2B-3, NS3, NS4A, NS4B, and NS5. Screening results indicated that three MAbs (DB21-6, DB22-4, and DB36-2) recognized E protein and another three MAbs (DB5-2, DB11-3, and DB31-4) recognized C protein. The identification and characterization of the 32 MAbs is summarized in Table 1.

(3) Dissection of DENV-2 MAbs Against Domain I-II or Domain III of E Protein

The DENV E protein is approximately 500 amino acids in length with N-terminal 400 amino acids forming the ectodomain (Modis et al., 2003). The E protein ectodomain consists of three domains: E-DI, E-DII, and E-DIII. E-DI-II is discontinuous and comprises residues 1-295 of E protein, and E-DIII is continuous and comprises residues 296-394 of E protein (Modis et al., 2003). EDI-II-flag (36 kDa) and EDIII-flag (17 kDa) fusion proteins were produced in *E. coli* via recombinant technology. Epitopes recognized by neutralizing antibodies have been identified in all three domains of the E protein (Goncalvez et al., 2004; Gromowski and Barrett, 2007; Roehrig, 2003; Sukupolyi-Petty et al., 2007).

To characterize the antigenic structure of the DENV E protein, we constructed and expressed recombinant E-DI-II and E-DIII from DENV-2 in *E. coli* expression system. The resulting plasmid expressed E-DI-II and E-DIII with Flag tag and hexahistidine tag at the C-terminus as fusion proteins. Analysis by SDS-PAGE under reducing conditions showed E-DI-II to be 36 kDa, E-DIII to be 17 kDa. They could be recognized by antibody to Flag tag sequences and antibody to DENV-2 E protein. Western blot analysis and IFA showed that, of the 17 MAbs recognizing E protein (see Table 1), 10 MAbs bound to recombinant E protein, with 8 MAbs binding to E-DI-II and 2 MAbs (DB25-2 and DB32-6) binding to DIII. 4G2 recognized pan-flavivirus E-DI-II, and 3H5 recognized DENV-2 serotype-specific E-DIII. Both were used as positive controls. MAbs DB21-6 and DB22-4 could not be identified by Western blotting, but E-DI-II was recognized using IFA. However, 5 MAbs could not be identified by these two assays. A total of 10 MAbs (DB2-3, DB9-1, DB13-19, DB21-6, DB22-4, DB23-3, DB27-3, DB33-3, DB39-2, and DB42-3) targeted to E-DI-II and 2 MAbs (DB25-2 and DB32-6) recognized E-DIII (see Table 1).

(4) Detection of Serum Samples from Dengue Patients by Capture ELISA

MAb DB42-3 was cross-reactive with DENV-1, -2, -3, and -4. The MAb were able to detect DENV-2 infected serum samples from DHF and DF patients. The mean optical density at 490 nm (A$_{490}$) for normal human serum samples plus 3 times the standard deviation were used to determine the cutoff value. The sensitivity of anti-E IgG capture ELISA at acute and convalescent-phase serum samples were 90% (9/10) and 100% (10/10), respectively. The cutoff value at different dilution 1:100, 1:400, 1:1,600, and 1:3,200 were 0.35, 0.14, 0.08, and 0.06, respectively. The sensitivity of anti-E IgM capture ELISA at acute and convalescent-phase serum samples were 50% (5/10) and 80% (8/10), respectively. The cutoff values at dilutions 1:100, 1:400, 1:1,600, and 1:3,200 were 0.34, 0.15, 0.07, and 0.08, respectively. In contrast, serum samples from healthy adults were found to be negative. These results indicate that the MAb DB42-3 can be useful for serologic diagnosis of DENV infection.

(5) Neutralizing Activity In Vitro

We evaluated the ability of purified MAbs for their ability to block DENV-2 infection in BHK-21 cells using a PRNT. Ten MAbs had neutralizing activity with 50% PRNT (PRNT$_{50}$) concentrations ranging from 0.14 μg/ml to 33 μg/ml, whereas normal mouse IgG (NMIgG) had no neutralizing activity against DENV up to concentrations as high as 100 μg/ml (Table 1). 3H5, a well-known strongly neutralizing DENV-2 serotype-specific MAb, was used as a positive control. The DENV-2 PRNT$_{50}$ concentration of 3H5 was found to be 0.41 μg/ml and to completely inhibit the viral infection at a concentration of 11 μg/ml.

DB32-6 was found to be a DENV-2 serotype-specific MAb against E-DIII and to be the most efficient in neutralizing DENV-2 infection at a PRNT$_{50}$ concentration of 0.14 μg/ml. It also completely inhibited the infection at a concentration of 1.2 μg/ml. DB32-6 had stronger neutralizing activity than 3H5. DB25-2 was found to be a DENV-2 serotype-specific MAb against E-DIII and to neutralize DENV-2 at a PRNT$_{50}$ titer of 1.2 μg/ml. DB2-3 and DB23-3 were found to be DENV-2 serotype-specific MAbs against E-DI-II and to have significant neutralizing activity at a PRNT$_{50}$ titer of 1.2 μg/ml and 0.41 μg/ml, respectively (Table 1). The complex reactive MAb DB42-3 recognized E-DI-II and was found to be able to neutralize DENV-2 at a PRNT$_{50}$ titer of 3.7 μg/ml. Four serotype-specific MAbs, DB3-4, DB9-1, DB19-4, and DB24-2, neutralized DENV-2 infection at the same range of concentration at a PRNT$_{50}$ titer of 3.7 μg/ml (Table 1). Furthermore, 4G2 and DB13-19, which were found to be complex reactive MAbs, had low neutralizing activity at a PRNT$_{50}$ titer of 11 μg/ml and 33 μg/ml, respectively (Table 1). However, the MAbs DB21-6, DB22-4, DB27-3, DB33-3, DB37-1, and DB39-2 had no or low neutralizing activity (PRNT$_{50}$>33 μg/ml) against DENV-2 (Table 1).

These findings indicate that serotype-specific MAb DB32-6 against E-DIII was the most potent in neutralizing DENY infection. Some serotype-specific MAbs, i.e., DB2-3 and DB23-3 against E-DI-II and DB25-2 against E-DIII, showed strong neutralizing activity. See Table 1.

(6) MAbs Prevent DENV-2-Induced Lethality in Suckling Mice

In vivo protection assay of neutralizing MAbs was performed with ICR strain, 2-day-old suckling mice (Meiklejohn et al., 1952; Sabin and Schlesinger, 1945). Mice were inoculated intracerebrally with 20 μl of DENV-2-MAb mixture containing 1×10$^4$ plaque-forming units (25-fold LD$_{50}$) of DENV-2 and 10 μg/ml neutralizing MAb. The mice were observed for abnormal symptoms daily for 21 days. Notably, the non-neutralizing antibody NMIgG-treated group showed paralysis, ruffling and slowing of activity around 6-9 days. This was followed by severe sickness, with anorexia, asthenia, and death within 10-17 days. In contrast, DB32-6 protected 93% of mice from lethal challenge of DENV-2. The protection activities of MAbs 3H5, DB23-3, DB2-3, and DB25-2 produced a 75%, 76%, 72%, and 71% survival rates, respectively. DB42-3 and DB13-19 resulted in 46% and 28% survival rates, respectively. The neutralizing MAbs showed a significant delay to the onset of paralysis and death, relative to NMIgG.

To evaluate the therapeutic potential of the highly protective MAb DB32-6, we administered 100 μg/ml or 1 μg/ml to i.c. infected suckling mice. The survival rates were 100% and 89%, respectively. In comparison, 3H5 produced 82% and 40% survival rates, respectively. DB32-6 had stronger neutralizing and protection activity than the well-known strongly neutralizing 3H5.

These results suggest that these neutralizing MAbs can be used for the treatment and inhibition of DENV-2 infection.

(7) Analysis of V$_H$ and V$_L$ Sequences

To further develop these neutralizing MAbs for clinical use, we cloned and analyzed the V$_H$ and V$_L$ DNA sequences of these MAbs. The amino acid sequences in the V$_H$ and V$_L$ segment of these neutralizing MAbs are shown in FIG. 1. Sequences analysis demonstrated that the six MAbs were distinct. The amino acid sequences of FR1 to FR4 and CDR1 to CDR3 were determined. The closest reference gene is shown in table 2 below. It was interesting that the DB2-3 and DB23-3 clones shared use of the V$_H$1S137*01 and J$_H$4*01 gene segments, suggesting a particular fitness for binding of the DENV-2 by the CDR1/2 heavy-chain loops encoded by the V$_H$ and J$_H$ gene segments. However, the DB13-19, DB25-2, DB32-6, and DB42-3 differed in gene segments. These data suggest that recurrent optimization of binding affinity may occurs through multiple rounds of somatic hypermutation and selection in vivo.

TABLE 2

Genetic features of neutralizing MAbs.

| Gene seg-ments$^a$ | MAbs | | | | | |
|---|---|---|---|---|---|---|
| | DB2-3 | DB13-19 | DB23-3 | DB25-2 | DB32-6 | DB42-3 |
| V$_H$ | 1S137*01 | 5S4*01 | 1S137*01 | 2-5*01 | 14-3*02 | 5-9*04 |
| J$_H$ | 4*01 | 3*01 | 4*01 | 2*01 | 1*01 | 4*01 |
| V$_L$ | 1-110*01 | 6-23*01 | 1-117*01 | 6-32*01 | 3-2*01 | 1*01 |
| J$_L$ | 2*01 | 1*01 | 1*01 | 2*01 | 1*01 | 1*01 |

$^a$V$_H$, heavy chain V gene; J$_H$, heavy chain J gene; V$_L$, light chain V gene; J$_L$, light chain J gene.

(8) Identification of Neutralizing Epitopes

Phage display technique was used to identify the neutralizing epitopes of the neutralizing antobodies described above. After three rounds of phage display biopanning, the phage titers were increased to 85-fold (DB32-6) and 331-fold (DB25-2) compared with the first round. Individual phage clones from the third round of biopanning were randomly selected. ELISA was performed to determine whether the MAbs specifically recognized selected phage clones. Of 20 selected phage clones, 17 and 18 clones had significant enhancement of binding activity to DB32-6 and DB25-2, respectively. The selected phage clones PC32-6 and PC25-14 were specifically and dose dependently bound to DB32-6 and DB25-2, respectively, and did not react with control NMIgG.

Seventeen immunopositive phage clones that were highly reactive with DB32-6 were amplified, and phage DNAs were isolated for DNA sequencing. All of the phage clones displayed 12 amino acid (aa) residues (FIG. 2, left). Phage-displayed peptide sequences selected by DB32-6 had the consensus motifs of histidine (H)-lysine (K)-glutamic acid (E)-tryptophan (W)/tyrosine (Y)-histidine (H) (FIG. 2, left). Similarly, 17 immunopositive phage clones which were selected by DB32-6 using phage library displayed 7 amino acid residues also contained the consensus motif H-K-E-W/Y-H (FIG. 2, left). Interestingly, all phage-displayed peptides selected by DB32-6 and DB25-2 contained lysine (K) and glutamic acid (E), respectively (FIG. 2).

To further confirm the neutralizing epitopes, we developed various E protein epitope-specific knock-out VLPs and screened loss-of-binding VLP mutants for identification of critical recognition residues. Using this strategy, we found that DB32-6 lost its VLP binding activity when the residue K310 in the A-strand of E-DIII was changed to alanine (K310A) or glutamine (K310Q). Similarly, DB25-2 lost its VLP binding activity when E311 was changed to arginine (E311R) in the A-strand of E-DIII. Both the critical recognition residues K310 and E311 were located in the A-strand of E-DIII. We found that MAb 3H5 recognized residues K305, E383, and P384, as previously reported.

We combined phage display, computational structure analysis, and VLP mutant assays to identify the neutralizing epitopes. Notably, even the adjacent residues (K310 and E311) induced antibodies with different levels of neutralizing activity. Our data further confirmed epitopes in the A-strand of E-DIII are important for inducing neutralizing antibodies.

(9) Development of Humanized DB32-6 MAb

The CDRs of DB32-6 were grafted onto human IgG1 backbone to create humanized DB32-6 (hDB32-6). The hDB32-6 antibody was expressed in CHO-K1 cells and purified from culture supernatants. The hDB32-6 antibody maintained the specificity of murine DB32-6 (mDB32-6) against DENV-2. We established stable clones of hDB32-6. After selection, MAbs hDB32-6-30, hDB32-6-48, and hDB32-6-51 were found to demonstrate high binding activities. Comparing these MAbs, we found hDB32-6-48 to have the highest production. MAb hDB32-6-48 was dose-dependent against DENV-2 and E-DIII. The affinity was analyzed by surface plasmon resonance. Murine DB32-6 and hDB32-6-48 bound E-DIII of DENV-2 with a similar affinity (0.12 nM and 0.18 nM, respectively). The results revealed that humanized DB32-6 maintained the E protein binding affinity of DB32-6.

(10) DB32-6 Protected Mice Against DENV-2-Induced Mortality and Hemorrhage

Two mouse models were used to assess whether DB32-6 could efficiently protect mice against DENV-2 challenge. We established a suckling mice model to determine the protective activity of mDB32-6 and hDB32-6. In the suckling mice protection experiment, 10 μg/ml of mDB32-6 and hDB32-6-48 protected mice against DENV-2 challenge and produced survival rates of 96% and 92%, respectively. Mice treated with 1 μg/ml of mDB32-6, hDB32-6-48, and 3H5 had survival rates of 92%, 77%, and 37%, respectively.

To further evaluate therapeutic efficiency of MAbs, we administered 5 μg of MAb at day one after infection. The results revealed that MAbs mDB32-6, hDB32-6-48, and 3H5 treated group had survival rates of 96%, 94%, and 56%, respectively. However, none of the mice in control antibody normal human IgG (NHIgG)-treated group survived.

C57BL/6 mice were employed to explore whether DB32-6 neutralizes DENV-2 and prevents hemorrhage development. DENV-2 16681 was incubated with PBS or each antibody before inoculation. Notably, compared to virus preincubated with PBS, which induced severe hemorrhage development in 100% of mice, virus preincubated with mDB32-6 and hDB32-6-48 induced 0% hemorrhage development. Virus preincubated with NHIgG and 3H5 induced mild hemorrhage in 80% and 60% of the mice, respectively. Severe hemorrhage developed in mice infected by PBS- and NHIgG-treated virus and mild hemorrhage in mice infected by virus is pretreated with 3H5. Importantly, mDB32-6 and hDB32-6-48 completely neutralized the ability of DENV to induce hemorrhage. These results demonstrate that humanized DB32-6 has excellent neutralizing activity against DENV-2 and can be used as a therapeutic antibody for the prevention and treatment of DENV-2 infection.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

REFERENCES

Beasley, D. W., and Barrett, A. D. (2002). Identification of neutralizing epitopes within structural domain III of the West Nile virus envelope protein. J Virol 76, 13097-13100.

Chau, T. N., Quyen, N. T., Thuy, T. T., Tuan, N. M., Hoang, D. M., Dung, N. T., Lien le, B., Quy, N. T., Hieu, N. T., Hieu, L. T., et al. (2008). Dengue in Vietnamese infants—results of infection-enhancement assays correlate with age-related disease epidemiology, and cellular immune responses correlate with disease severity. J Infect Dis 198, 516-524.

Chen, Y. C., Huang, H. N., Lin, C. T., Chen, Y. F., King, C. C., and Wu, H. C. (2007). Generation and characterization of monoclonal antibodies against dengue virus type 1 for epitope mapping and serological detection by epitope-based peptide antigens. Clin Vaccine Immunol 14, 404-411.

Chen H C, Hofman F M, Kung J T, Lin Y D, Wu-Hsieh B A (2007) Both virus and tumor necrosis factor alpha are critical for endothelium damage in a mouse model of dengue virus-induced hemorrhage. J Virol 81: 5518-5526.

Churdboonchart, V., Bhamarapravati, N., Peampramprecha, S., and Sirinavin, S. (1991). Antibodies against dengue viral proteins in primary and secondary dengue hemorrhagic fever. Am J Trop Med Hyg 44, 481-493.

Crill, W. D., and Chang, G. J. (2004). Localization and characterization of flavivirus envelope glycoprotein cross-reactive epitopes. J Virol 78, 13975-13986.

Crill, W. D., Hughes, H. R., Delorey, M. J., and Chang, G. J. (2009). Humoral immune responses of dengue fever patients using epitope-specific serotype-2 virus-like particle antigens. PLoS One 4, e4991.

Crill, W. D., and Roehrig, J. T. (2001). Monoclonal antibodies that bind to domain III of dengue virus E glycoprotein are the most efficient blockers of virus adsorption to Vero cells. J Virol 75, 7769-7773.

Dubel, S., Breitling, F., Fuchs, P., Zewe, M., Gotter, S., Welschof, M., Moldenhauer, G., and Little, M. (1994). Isolation of IgG antibody Fv-DNA from various mouse and rat hybridoma cell lines using the polymerase chain reaction with a simple set of primers. J Immunol Methods 175, 89-95.

Falgout, B., Bray, M., Schlesinger, J. J., and Lai, C. J. (1990). Immunization of mice with recombinant vaccinia virus expressing authentic dengue virus nonstructural protein NS1 protects against lethal dengue virus encephalitis. J Virol 64, 4356-4363.

Farrar, J., Focks, D., Gubler, D., Barrera, R., Guzman, M. G., Simmons, C., Kalayanarooj, S., Lum, L., McCall, P. J., Lloyd, L., et al. (2007). Towards a global dengue research agenda. Trop Med Int Health 12, 695-699.

Flamand, M., Megret, F., Mathieu, M., Lepault, J., Rey, F. A., and Deubel, V. (1999). Dengue virus type 1 nonstructural glycoprotein NS1 is secreted from mammalian cells as a soluble hexamer in a glycosylation-dependent fashion. J Virol 73, 6104-6110.

Goncalvez, A. P., Chien, C. H., Tubthong, K., Gorshkova, I., Roll, C., Donau, O., Schuck, P., Yoksan, S., Wang, S. D., Purcell, R. H., et al. (2008). Humanized monoclonal antibodies derived from chimpanzee Fabs protect against Japanese encephalitis virus in vitro and in vivo. J Virol 82, 7009-7021.

Goncalvez, A. P., Purcell, R. H., and Lai, C. J. (2004). Epitope determinants of a chimpanzee Fab antibody that efficiently cross-neutralizes dengue type 1 and type 2 viruses map to inside and in close proximity to fusion loop of the dengue type 2 virus envelope glycoprotein. J Virol 78, 12919-12928.

Green, S., and Rothman, A. (2006). Immunopathological mechanisms in dengue and dengue hemorrhagic fever. Curr Opin Infect Dis 19, 429-436.

Gromowski, G. D., and Barrett, A. D. (2007). Characterization of an antigenic site that contains a dominant, type-specific neutralization determinant on the envelope protein domain III (ED3) of dengue 2 virus. Virology 366, 349-360.

Gromowski, G. D., Barrett, N. D., and Barrett, A. D. (2008). Characterization of dengue virus complex-specific neutralizing epitopes on envelope protein domain III of dengue 2 virus. J Virol 82, 8828-8837.

Gubler, D. J. (1998). Dengue and dengue hemorrhagic fever. Clin Microbiol Rev 11, 480-496.

Halstead, S. B. (1988). Pathogenesis of dengue: challenges to molecular biology. Science 239, 476-481.

Halstead, S. B. (2007). Dengue. Lancet 370, 1644-1652.

Halstead, S. B., and O'Rourke, E. J. (1977). Antibody-enhanced dengue virus infection in primate leukocytes. Nature 265, 739-741.

Kalayanarooj, S., Vaughn, D. W., Nimmannitya, S., Green, S., Suntayakorn, S., Kunentrasai, N., Viramitrachai, W., Ratanachu-eke, S., Kiatpolpoj, S., Innis, B. L., et al. (1997). Early clinical and laboratory indicators of acute dengue illness. J Infect Dis 176, 313-321.

Kuhn, R. J., Zhang, W., Rossmann, M. G., Pletnev, S. V., Corver, J., Lenches, E., Jones, C. T., Mukhopadhyay, S., Chipman, P. R., Strauss, E. G., et al. (2002). Structure of dengue virus: implications for flavivirus organization, maturation, and fusion. Cell 108, 717-725.

Lai, C. J., Goncalvez, A. P., Men, R., Wernly, C., Donau, O., Engle, R. E., and Purcell, R. H. (2007). Epitope determinants of a chimpanzee dengue virus type 4 (DENV-4)-neutralizing antibody and protection against DENV-4 challenge in mice and rhesus monkeys by passively transferred humanized antibody. J Virol 81, 12766-12774.

Lai, C. Y., Tsai, W. Y., Lin, S. R., Kao, C. L., Hu, H. P., King, C. C., Wu, H. C., Chang, G. J., and Wang, W. K. (2008). Antibodies to envelope glycoprotein of dengue virus during the natural course of infection are predominantly cross-reactive and recognize epitopes containing highly conserved residues at the fusion loop of domain II. J Virol 82, 6631-6643.

Lanciotti, R. S., Calisher, C. H., Gubler, D. J., Chang, G. J., and Vorndam, A. V. (1992). Rapid detection and typing of dengue viruses from clinical samples by using reverse transcriptase-polymerase chain reaction. J Clin Microbiol 30, 545-551.

Lefranc, M. P., Giudicelli, V., Ginestoux, C., Jabado-Michaloud, J., Folch, G., Bellahcene, F., Wu, Y., Gemrot, E., Brochet, X., Lane, J., et al. (2009). IMGT, the international ImMunoGeneTics information system. Nucleic Acids Res 37, D1006-1012.

Lin, B., Parrish, C. R., Murray, J. M., and Wright, P. J. (1994). Localization of a neutralizing epitope on the envelope protein of dengue virus type 2. Virology 202, 885-890.

Lin, C. F., Chiu, S. C., Hsiao, Y. L., Wan, S. W., Lei, H. Y., Shiau, A. L., Liu, H. S., Yeh, T. M., Chen, S. H., Liu, C. C., et al. (2005). Expression of cytokine, chemokine, and adhesion molecules during endothelial cell activation induced by antibodies against dengue virus nonstructural protein 1. J Immunol 174, 395-403.

Lin, C. F., Lei, H. Y., Shiau, A. L., Liu, H. S., Yeh, T. M., Chen, S. H., Liu, C. C., Chiu, S. C., and Lin, Y. S. (2002). Endothelial cell apoptosis induced by antibodies against dengue virus nonstructural protein 1 via production of nitric oxide. J Immunol 169, 657-664.

Lindenbach, B. D., and Rice, C. M. (1997). trans-Complementation of yellow fever virus NS1 reveals a role in early RNA replication. J Virol 71, 9608-9617.

Lindenbach, B. D., and Rice, C. M. (1999). Genetic interaction of flavivirus nonstructural proteins NS1 and NS4A as a determinant of replicase function. J Virol 73, 4611-4621.

Littaua, R., Kurane, I., and Ennis, F. A. (1990). Human IgG Fc receptor II mediates antibody-dependent enhancement of dengue virus infection. J Immunol 144, 3183-3186.

Mathew, A., and Rothman, A. L. (2008). Understanding the contribution of cellular immunity to dengue disease pathogenesis. Immunol Rev 225, 300-313.

Meiklejohn, G., England, B., and Lennette (1952). Propagation of dengue virus strains in unweaned mice. Am J Trop Med Hyg 1, 51-58.

Modis, Y., Ogata, S., Clements, D., and Harrison, S. C. (2003). A ligand-binding pocket in the dengue virus envelope glycoprotein. Proc Natl Acad Sci USA 100, 6986-6991.

Modis, Y., Ogata, S., Clements, D., and Harrison, S. C. (2005). Variable surface epitopes in the crystal structure of dengue virus type 3 envelope glycoprotein. J Virol 79, 1223-1231.

Mukhopadhyay, S., Kuhn, R. J., and Rossmann, M. G. (2005). A structural perspective of the flavivirus life cycle. Nat Rev Microbiol 3, 13-22.

Normile, D. (2007). Tropical diseases. Hunt for dengue vaccine heats up as the disease burden grows. Science 317, 1494-1495.

Oliphant, T., Engle, M., Nybakken, G. E., Doane, C., Johnson, S., Huang, L., Gorlatov, S., Mehlhop, E., Marri, A., Chung, K. M., et al. (2005). Development of a humanized monoclonal antibody with therapeutic potential against West Nile virus. Nat Med 11, 522-530.

Oliphant, T., Nybakken, G. E., Engle, M., Xu, Q., Nelson, C. A., Sukupolyi-Petty, S., Marri, A., Lachmi, B. E., Olshevsky, U., Fremont, D. H., et al. (2006). Antibody recognition and neutralization determinants on domains I and II of West Nile Virus envelope protein. J Virol 80, 12149-12159.

Orlandi, R., Gussow, D. H., Jones, P. T., and Winter, G. (1989). Cloning immunoglobulin variable domains for expression by the polymerase chain reaction. Proc Natl Acad Sci USA 86, 3833-3837.

Orum, H., Andersen, P. S., Oster, A., Johansen, L. K., Riise, E., Bjornvad, M., Svendsen, I., and Engberg, J. (1993). Efficient method for constructing comprehensive murine Fab antibody libraries displayed on phage. Nucleic Acids Res 21, 4491-4498.

Pierson, T. C., Fremont, D. H., Kuhn, R. J., and Diamond, M. S. (2008). Structural insights into the mechanisms of antibody-mediated neutralization of flavivirus infection: implications for vaccine development. Cell Host Microbe 4, 229-238.

Pokidysheva, E., Zhang, Y., Battisti, A. J., Bator-Kelly, C. M., Chipman, P. R., Xiao, C., Gregorio, G. G., Hendrickson, W. A., Kuhn, R. J., and Rossmann, M. G. (2006). Cryo-EM reconstruction of dengue virus in complex with the carbohydrate recognition domain of DC-SIGN. Cell 124, 485-493.

Qu, X., Chen, W., Maguire, T., and Austin, F. (1993). Immunoreactivity and protective effects in mice of a recombinant dengue 2 Tonga virus NS1 protein produced in a baculovirus expression system. J Gen Virol 74 (Pt 1), 89-97.

Rey, F. A., Heinz, F. X., Mandl, C., Kunz, C., and Harrison, S. C. (1995). The envelope glycoprotein from tick-borne encephalitis virus at 2 A resolution. Nature 375, 291-298.

Rice, C. M., Lenches, E. M., Eddy, S. R., Shin, S. J., Sheets, R. L., and Strauss, J. H. (1985). Nucleotide sequence of yellow fever virus: implications for flavivirus gene expression and evolution. Science 229, 726-733.

Roehrig, J. T. (2003). Antigenic structure of flavivirus proteins. Adv Virus Res 59, 141-175.

Roehrig, J. T., Bolin, R. A., and Kelly, R. G. (1998). Monoclonal antibody mapping of the envelope glycoprotein of the dengue 2 virus, Jamaica. Virology 246, 317-328.

Sabin, A. B., and Schlesinger, R. W. (1945). Production of Immunity to Dengue with Virus Modified by Propagation in Mice. Science 101, 640-642.

Schlesinger, J. J., Brandriss, M. W., Putnak, J. R., and Walsh, E. E. (1990). Cell surface expression of yellow fever virus non-structural glycoprotein NS1: consequences of interaction with antibody. J Gen Virol 71 (Pt 3), 593-599.

Sukupolyi-Petty, S., Austin, S. K., Purtha, W. E., Oliphant, T., Nybakken, G. E., Schlesinger, J. J., Roehrig, J. T., Gromowski, G. D., Barrett, A. D., Fremont, D. H., et al. (2007). Type- and subcomplex-specific neutralizing antibodies against domain III of dengue virus type 2 envelope protein recognize adjacent epitopes. J Virol 81, 12816-12826.

Throsby, M., Geuijen, C., Goudsmit, J., Bakker, A. Q., Korimbocus, J., Kramer, R. A., Clijsters-van der Horst, M., de Jong, M., Jongeneelen, M., Thijsse, S., et al. (2006). Isolation and characterization of human monoclonal antibodies from individuals infected with West Nile Virus. J Virol 80, 6982-6992.

Valdes, K., Alvarez, M., Pupo, M., Vazquez, S., Rodriguez, R., and Guzman, M. G. (2000). Human Dengue antibodies against structural and nonstructural proteins. Clin Diagn Lab Immunol 7, 856-857.

Vaughn, D. W., Green, S., Kalayanarooj, S., Innis, B. L., Nimmannitya, S., Suntayakorn, S., Endy, T. P., Raengsakulrach, B., Rothman, A. L., Ennis, F. A., et al. (2000). Dengue viremia titer, antibody response pattern, and virus serotype correlate with disease severity. J Infect Dis 181, 2-9.

Vaughn, D. W., Nisalak, A., Kalayanarooj, S., Solomon, T., Dung, N. M., Cuzzubbo, A., and Devine, P. L. (1998). Evaluation of a rapid immunochromatographic test for diagnosis of dengue virus infection. J Clin Microbiol 36, 234-238.

Vaughn, D. W., Nisalak, A., Solomon, T., Kalayanarooj, S., Nguyen, M. D., Kneen, R., Cuzzubbo, A., and Devine, P. L. (1999). Rapid serologic diagnosis of dengue virus infection using a commercial capture ELISA that distinguishes primary and secondary infections. Am J Trop Med Hyg 60, 693-698.

Wang, W. K., Chen, H. L., Yang, C. F., Hsieh, S. C., Juan, C. C., Chang, S. M., Yu, C. C., Lin, L. H., Huang, J. H., and King, C. C. (2006). Slower rates of clearance of viral load and virus-containing immune complexes in patients with dengue hemorrhagic fever. Clin Infect Dis 43, 1023-1030.

Winkler, G., Maxwell, S. E., Ruemmler, C., and Stollar, V. (1989). Newly synthesized dengue-2 virus nonstructural protein NS1 is a soluble protein but becomes partially hydrophobic and membrane-associated after dimerization. Virology 171, 302-305.

Wu, H. C., Huang, Y. L., Chao, T. T., Jan, J. T., Huang, J. L., Chiang, H. Y., King, C. C., and Shaio, M. F. (2001). Identification of B-cell epitope of dengue virus type 1 and its application in diagnosis of patients. J Clin Microbiol 39, 977-982.

Wu, H. C., Jung, M. Y., Chiu, C. Y., Chao, T. T., Lai, S. C., Jan, J. T., and Shaio, M. F. (2003). Identification of a dengue virus type 2 (DEN-2) serotype-specific B-cell epitope and detection of DEN-2-immunized animal serum samples using an epitope-based peptide antigen. J Gen Virol 84, 2771-2779.

Yen Y T, Chen H C, Lin Y D, Shieh C C, Wu-Hsieh B A (2008) Enhancement by tumor necrosis factor alpha of dengue virus-induced endothelial cell production of reactive nitrogen and oxygen species is key to hemorrhage development. J Virol 82: 12312-12324.

Yu, C. Y., Hsu, Y. W., Liao, C. L., and Lin, Y. L. (2006). Flavivirus infection activates the XBP1 pathway of the unfolded protein response to cope with endoplasmic reticulum stress. J Virol 80, 11868-11880.

Zhang, Y., Corver, J., Chipman, P. R., Zhang, W., Pletnev, S. V., Sedlak, D., Baker, T. S., Strauss, J. H., Kuhn, R. J., and Rossmann, M. G. (2003). Structures of immature flavivirus particles. EMBO J 22, 2604-2613.

What is claimed is:

1. An isolated antibody that specifically binds dengue virus serotype 2 envelope domain III, the antibody comprising a heavy chain CDR 1 including SEQ ID NO:2, a heavy chain CDR2 including SEQ ID NO:3, a heavy chain CDR3 including SEQ ID NO:4, a light chain CDR1 including SEQ ID NO:6, a light chain CDR2 including SEQ ID NO:7, and a light chain CDR3 including SEQ ID NO:8.

2. The isolated antibody of claim 1, the antibody comprising a heavy chain variable region including SEQ ID NO:1 and a light chain variable region including SEQ ID NO:5.

3. The isolated antibody of claim 1, wherein the antibody is an antigen-binding fragment.

4. The isolated antibody of claim 1, wherein the antibody is humanized.

5. The isolated antibody of claim 1, wherein the antibody is a chimeric antibody.

6. The isolated antibody of claim 1, wherein the antibody is a single-chain antibody.

7. The isolated antibody of claim 3, wherein the antigen-binding fragment is a F(ab')$_2$, Fab, or Fv.

8. A method for treating dengue virus serotype 2 infection, the method comprising administering to a subject in need thereof an effective amount of the antibody of claim 1.

9. The method of claim 8, wherein the antibody includes a heavy chain variable region including SEQ ID NO:1 and a light chain variable region including SEQ ID NO:5.

10. The method of claim 8, wherein the antibody is humanized.

11. A method for detecting presence of a dengue virus antigen in a sample, the method comprising
    providing a sample suspected of containing a dengue virus antigen,
    contacting the sample with the antibody of claim 1, and
    determining whether the antibody binds to an antigen in the sample, wherein binding of the antibody to the antigen indicates presence of a dengue virus antigen in the sample, the antigen being dengue virus serotype 2 envelope domain III.

12. The method of claim 11, wherein the antibody includes a heavy chain variable region including SEQ ID NO:1 and a light chain variable region including SEQ ID NO:5.

13. The method of claim 11, wherein the antibody is humanized.

14. The method of claim 11, wherein the sample is a tissue sample from a patient suspected of having dengue virus infection.

15. The method of claim 11, wherein the sample is a serum sample from a patient suspected of having dengue virus infection.

* * * * *

SEQUENCE LISTING

```
<160> NUMBER OF SEQ ID NOS: 35

<210> SEQ ID NO 1
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 1

Gln Val Gln Leu Gln Gln Ser Gly Ala Glu Leu Val Lys Pro Gly Ala
1               5                   10                  15
```

```
Ser Val Lys Leu Ser Cys Thr Ala Ser Gly Phe Asn Ile Lys Asp Thr
            20                  25                  30

Tyr Ile His Trp Val Lys Gln Arg Pro Gly Gln Gly Leu Glu Trp Ile
        35                  40                  45

Gly Arg Ile Asp Pro Glu Asn Gly Asn Ala Lys Tyr Asp Pro Asn Phe
    50                  55                  60

Gln Ala Lys Ala Thr Ile Thr Ala Asp Thr Ser Ser Asn Thr Ala Tyr
65                  70                  75                  80

Leu His Leu Ser Ser Leu Thr Ser Glu Asp Thr Ala Val Tyr Tyr Ser
                85                  90                  95

Val Arg Thr Gly Ser Phe Trp Tyr Phe Asp Val Trp Gly Ala Gly Thr
            100                 105                 110

Thr Val Thr Val Ser Ser
        115

<210> SEQ ID NO 2
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 2

Phe Asn Ile Lys Asp Thr Tyr Ile His
1               5

<210> SEQ ID NO 3
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 3

Gly Arg Ile Asp Pro Glu Asn Gly Asn Ala Lys Tyr Asp Pro Asn Phe
1               5                   10                  15

Gln Ala Lys Ala
            20

<210> SEQ ID NO 4
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 4

Val Arg Thr Gly Ser Phe Trp Tyr Phe Asp Val
1               5                   10

<210> SEQ ID NO 5
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 5

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Lys Tyr
            20                  25                  30
```

```
Gly Ile Thr Phe Leu Asn Trp Phe Gln Gln Lys Pro Gly Gln Pro Pro
        35                  40                  45

Lys Leu Leu Ile His Ser Ala Ser Asn Arg Gly Ser Gly Val Pro Ala
 50                  55                  60

Arg Phe Ser Gly Ser Gly Ser Gly Thr Asp Phe Ser Leu Asn Ile His
 65                  70                  75                  80

Pro Met Glu Glu Asp Asp Ile Ala Met Tyr Phe Cys Gln Gln Ser Lys
                 85                  90                  95

Glu Val Pro Trp Thr Phe Gly Gly Gly Thr Lys Leu Glu Ile Lys
                100                 105                 110

<210> SEQ ID NO 6
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 6

Arg Ala Ser Glu Ser Val Asp Lys Tyr Gly Ile Thr Phe Leu Asn
 1               5                  10                  15

<210> SEQ ID NO 7
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 7

Ser Ala Ser Asn Arg Gly Ser
 1               5

<210> SEQ ID NO 8
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 8

Gln Gln Ser Lys Glu Val Pro Trp Thr
 1               5

<210> SEQ ID NO 9
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 9
gatgctagca tgcgttgcat aggaata                                          27

<210> SEQ ID NO 10
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 10
gatctcgagt cctttgagct gtagttt                                          27

<210> SEQ ID NO 11
```

```
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 11
gatgctagca tgaaaggaat gtcatac                                          27

<210> SEQ ID NO 12
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 12
gatctcgagt tggccgatag aact                                             24

<210> SEQ ID NO 13
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 13

Glu Val Gln Leu Gln Gln Ser Gly Ala Glu Leu Val Arg Pro Gly Val
 1               5                  10                  15

Ser Val Lys Ile Ser Cys Lys Gly Ser Gly Tyr Thr Phe Thr Asp Tyr
            20                  25                  30

Ala Ile Thr Trp Val Lys Glu Ser His Ala Lys Ser Leu Glu Trp Ile
        35                  40                  45

Gly Leu Ile Ser Thr Tyr Tyr Gly Asp Ser Phe Tyr Asn Gln Lys Phe
    50                  55                  60

Lys Gly Lys Ala Thr Met Thr Val Asp Lys Ser Ser Arg Thr Ala Tyr
65                  70                  75                  80

Met Glu Leu Ala Arg Leu Thr Ser Glu Asp Ser Ala Ile Tyr Tyr Cys
                85                  90                  95

Thr Ile Arg Asp Gly Lys Gly Ala Met Asp Tyr Trp Gly Gln Gly Thr
            100                 105                 110

Ser Val Thr Val Ser Ser
        115

<210> SEQ ID NO 14
<211> LENGTH: 129
<212> TYPE: PRT
<213> ORGANISM: Artificial sequence
<220> FEATURE:
<223> OTHER INFORMATION: Synthetic polypeptide

<400> SEQUENCE: 14

Glu Val Lys Leu Val Glu Ser Gly Gly Gly Leu Val Lys Pro Gly Gly
 1               5                  10                  15

Ser Leu Lys Leu Ser Cys Ala Thr Ser Gly Phe Thr Phe Ser Thr Tyr
            20                  25                  30

Gly Met Ser Trp Val Arg Gln Thr Pro Glu Lys Arg Leu Glu Trp Val
        35                  40                  45

Ala Thr Ile Ser Gly Asp Gly Ser Tyr Thr Tyr Tyr Pro Asp Thr Val
    50                  55                  60

Lys Gly Arg Phe Thr Ile Ser Arg Asp Asn Ala Lys Asn Asn Leu Tyr
65                  70                  75                  80
```

Leu Gln Met Ser Ser Leu Arg Ser Glu Asp Thr Ala Leu Tyr Tyr Cys
                85                  90                  95

Ala Ser Tyr Asn Tyr Gly Gly Phe Ala Tyr Trp Gly Gln Gly Thr Leu
            100                 105                 110

Val Ser Val Ser Ala Ala Lys Thr Thr Pro Pro Ser Asp Tyr Pro Leu
            115                 120                 125

Ala

<210> SEQ ID NO 15
<211> LENGTH: 128
<212> TYPE: PRT
<213> ORGANISM: Artificial sequence
<220> FEATURE:
<223> OTHER INFORMATION: Synthetic polypeptide

<400> SEQUENCE: 15

Glu Val Gln Leu Gln Gln Ser Gly Ser Glu Leu Val Arg Pro Gly Val
1               5                   10                  15

Ser Val Lys Ile Ser Cys Lys Gly Ser Gly Tyr Thr Phe Thr Asp Tyr
                20                  25                  30

Ala His Trp Val Arg Gln Ser His Asp Lys Ser Leu Glu Trp Ile Gly
            35                  40                  45

Leu Ile Ser Thr Tyr Tyr Gly Asp Val Ser Tyr Asn Gln Lys Phe Lys
        50                  55                  60

Gly Lys Ala Thr Thr Val Asp Lys Ser Ser Thr Ala Tyr Leu Glu
65                  70                  75                  80

Leu Ala Arg Leu Thr Ser Glu Asp Ser Ala Ile Tyr Tyr Cys Ala Arg
                85                  90                  95

Leu Gly Gly Asp Phe Phe Ala Asp Tyr Trp Gly Gln Gly Thr Ser Val
            100                 105                 110

Thr Val Ser Ser Ala Lys Thr Thr Pro Pro Ser Asp Tyr Pro Leu Ala
            115                 120                 125

<210> SEQ ID NO 16
<211> LENGTH: 124
<212> TYPE: PRT
<213> ORGANISM: Artificial sequence
<220> FEATURE:
<223> OTHER INFORMATION: Synthetic polypeptide

<400> SEQUENCE: 16

Gln Val Gln Leu Lys Glu Ser Gly Pro Gly Leu Val Gln Pro Ser Gln
1               5                   10                  15

Ser Leu Ser Ile Thr Cys Thr Val Ser Gly Phe Ser Leu Thr Asp Tyr
                20                  25                  30

Gly Val His Trp Ile Arg Gln Ser Pro Gly Lys Gly Leu Glu Trp Leu
            35                  40                  45

Gly Val Ile Trp Arg Gly Gly Ile Thr Asp Tyr Asn Ala Ala Phe Met
        50                  55                  60

Ser Arg Leu Ser Ile Thr Lys Asp Asn Ser Lys Ser Gln Val Phe Phe
65                  70                  75                  80

Lys Met Asp Ser Leu Gln Pro Asp Asp Ser Ala Ile Tyr Tyr Cys Ala
                85                  90                  95

Lys Asn Phe Gly Thr His Tyr Tyr Gly Ser Asn Tyr Gly Asn Phe Asp
            100                 105                 110

Tyr Trp Gly Gln Gly Thr Thr Leu Thr Val Ser Ser
            115                 120

```
<210> SEQ ID NO 17
<211> LENGTH: 134
<212> TYPE: PRT
<213> ORGANISM: Artificial sequence
<220> FEATURE:
<223> OTHER INFORMATION: Synthetic polypeptide

<400> SEQUENCE: 17

Glu Val Lys Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Asn Phe
            20                  25                  30

Ala Met Ser Trp Val Arg Gln Thr Pro Glu Lys Arg Leu Glu Trp Val
        35                  40                  45

Ala Thr Ile Gly Gly Gly Asp Ser Tyr Phe Pro Asp Ser Val Lys
    50                  55                  60

Gly Arg Phe Thr Ile Ser Arg Asp Asn Ala Arg Asn Ile Leu Tyr Leu
65                  70                  75                  80

Gln Met Ser Ser Leu Arg Ser Asp Asp Thr Ala Met Tyr Phe Cys Thr
                85                  90                  95

Arg Glu Gly Gly Asp Asp Asp Gln Tyr Tyr Tyr Ser Met Asp Tyr Trp
            100                 105                 110

Gly Gln Gly Thr Ser Val Thr Val Ser Ser Ala Lys Thr Thr Pro Pro
        115                 120                 125

Ser Asp Tyr Pro Leu Ala
    130

<210> SEQ ID NO 18
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 18

Asp Val Val Met Thr Gln Thr Pro Leu Ser Leu Pro Val Ser Leu Gly
1               5                   10                  15

Asp Leu Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asn Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Gly Gly Gly Thr Lys Leu Glu Ile Lys
            100                 105                 110

<210> SEQ ID NO 19
<211> LENGTH: 116
<212> TYPE: PRT
<213> ORGANISM: Artificial sequence
<220> FEATURE:
<223> OTHER INFORMATION: Synthetic polypeptide

<400> SEQUENCE: 19

Asp Ile Val Met Thr Gln Ser His Lys Phe Met Ser Thr Ser Val Gly
1               5                   10                  15
```

```
Asp Arg Val Ser Ile Thr Cys Lys Ala Ser Gln Asp Val Gly Ile Ala
            20                  25                  30

Val Ala Trp Tyr Gln Gln Lys Pro Arg Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Leu Thr Leu Thr Ile Asn Asn Val Gln Ser
65                  70                  75                  80

Glu Asp Leu Ala Asp Tyr Phe Cys Gln Gln Phe Asn Ser Tyr Pro Leu
                85                  90                  95

Thr Phe Gly Gly Gly Thr Lys Leu Glu Ile Lys Arg Ala Asp Ala Ala
            100                 105                 110

Pro Thr Val Ser
        115

<210> SEQ ID NO 20
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 20

Asp Val Leu Thr Gln Thr Pro Leu Ser Leu Pro Val Ser Leu Gly Asp
1               5                   10                  15

Gln Ala Ser Ile Ser Cys Arg Ser Ser Gln Ser Val Val Asn Ser Asn
            20                  25                  30

Gly Asn Thr Tyr Leu Glu Trp Tyr Leu Gln Lys Pro Gly Gln Ser Pro
        35                  40                  45

Lys Leu Leu Ile Tyr Lys Val Ser Asn Arg Phe Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Leu Gly Val Tyr Tyr Cys Phe Gln Gly Ser
                85                  90                  95

His Phe Pro Arg Thr Phe Gly Gly Gly Thr Lys Leu Glu Ile Lys Arg
            100                 105                 110

Ala Asp Ala Ala Pro Thr Val Ser
            115                 120

<210> SEQ ID NO 21
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 21

Val Val Met Thr Gln Thr Pro Lys Phe Leu Leu Val Ser Ala Gly Asp
1               5                   10                  15

Arg Val Thr Ile Thr Cys Lys Ala Ser Gln Ser Val Ser Asn Asp Val
            20                  25                  30

Ala Trp Tyr Gln Gln Lys Pro Gly Gln Ser Pro Lys Leu Leu Ile Tyr
        35                  40                  45

Tyr Val Ser Asn Arg Tyr Ser Gly Val Pro Asp Arg Phe Thr Gly Ser
    50                  55                  60

Gly Tyr Gly Thr Asp Phe Thr Phe Thr Ile Asn Thr Val Gln Ala Glu
65                  70                  75                  80
```

-continued

Asp Leu Ala Val Tyr Phe Cys Gln Gln Asp Tyr Ser Ser Pro Tyr Thr
                85                  90                  95

Phe Gly Gly Gly Thr Lys Leu Glu Ile Lys
            100                 105

<210> SEQ ID NO 22
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 22

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp Arg Leu Phe Asn Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Pro Glu Asp Glu Ala Ile Tyr Phe Cys Ala Leu Trp Tyr Ser Asn
                85                  90                  95

His Phe Trp Val Phe Gly Gly Gly Thr Lys Leu Thr Val Leu Gly Gln
            100                 105                 110

Pro Lys Ser Thr Pro Thr Leu Thr
        115                 120

<210> SEQ ID NO 23
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 23

Phe His Lys Glu Tyr His Ile Thr Arg Met Thr Ala
1               5                   10

<210> SEQ ID NO 24
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 24

Thr His Lys Glu Tyr His Thr Leu Met Gly Leu Gln
1               5                   10

<210> SEQ ID NO 25
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 25

Tyr His Lys Glu Trp His Gly Ser Leu Leu Ala Arg
1               5                   10

```
<210> SEQ ID NO 26
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 26

Asn His Lys Thr Trp His Leu Gln Val Asn Pro Leu
1               5                   10

<210> SEQ ID NO 27
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 27

Thr His Lys Leu Trp His Ile Pro Ser Asn Trp Arg
1               5                   10

<210> SEQ ID NO 28
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 28

Thr His Lys Glu Tyr His Trp
1               5

<210> SEQ ID NO 29
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 29

Ser His Lys Glu Trp His Val
1               5

<210> SEQ ID NO 30
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 30

Met His Lys Glu Trp His Leu
1               5

<210> SEQ ID NO 31
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 31

Val Pro Gln Leu Gly Trp Trp Tyr Asp Glu Pro Thr
1               5                   10

<210> SEQ ID NO 32
```

-continued

```
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 32

Thr Phe His Trp Ser Pro Trp Pro Trp Leu Asp Glu
1               5                   10

<210> SEQ ID NO 33
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 33

Asn Ala Leu Tyr Met Ile Arg Leu Ser Ser Glu
1               5                   10

<210> SEQ ID NO 34
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 34

Tyr Ser Ser Glu Trp Tyr Thr Val Pro Leu Pro Leu
1               5                   10

<210> SEQ ID NO 35
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 35

Ser His Arg Trp Val Glu Trp Arg Asn Phe Phe Pro
1               5                   10
```